United States Patent [19]

Tobey

[11] Patent Number: 5,281,584

[45] Date of Patent: Jan. 25, 1994

[54] EFFECT OF PARTICLE-SIZE DISTRIBUTION OF CELLULOSE ETHERS ON PALATABILITY OF COMPOSITIONS

[75] Inventor: Stephen W. Tobey, Midland, Mich.

[73] Assignee: The Dow Chemical Company, Midland, Mich.

[21] Appl. No.: 843,748

[22] Filed: Feb. 28, 1992

[51] Int. Cl.⁵ .................. A21D 10/02; A21D 2/08; A23L 1/0534; A61K 31/715

[52] U.S. Cl. .......................... 514/57; 514/781; 514/884; 424/439; 424/442; 426/804; 426/549

[58] Field of Search .............. 514/57, 781, 884; 424/439, 442; 426/804, 549

[56] References Cited

U.S. PATENT DOCUMENTS

| | | | |
|---|---|---|---|
| 2,802,741 | 8/1957 | Weaver et al. | 99/94 |
| 3,689,652 | 9/1972 | Curran et al. | 544/239 |
| 3,709,876 | 1/1973 | Glomski et al. | 260/231 A |
| 3,974,272 | 8/1976 | Polli et al. | 424/78.12 |
| 4,251,519 | 2/1981 | Robbins et al. | 424/180 |
| 4,265,879 | 5/1981 | Fields et al. | 424/78 |
| 4,284,649 | 8/1981 | Wiczer | 424/362 |
| 4,326,523 | 4/1982 | Wolfrom et al. | 128/260 |
| 4,362,711 | 12/1982 | Cerami | 424/33 |
| 4,451,490 | 5/1984 | Silverman et al. | 426/553 |
| 4,614,545 | 9/1986 | Hess | 536/88 |
| 4,626,287 | 12/1986 | Shah et al. | 106/197.1 |
| 4,704,285 | 11/1987 | Alderman | 424/468 |
| 4,729,895 | 3/1988 | Makino et al. | 424/465 |
| 4,732,917 | 3/1988 | Shah et al. | 514/781 |
| 4,734,285 | 3/1988 | Alderman | 424/468 |
| 4,754,027 | 6/1988 | Applegren | 536/114 |
| 4,789,664 | 12/1988 | Seligson et al. | 514/23 |
| 4,820,813 | 4/1989 | Schultz | 536/84 |
| 4,846,889 | 7/1989 | Meyer | 106/115 |
| 4,849,222 | 7/1989 | Broaddus | 424/195.1 |
| 4,883,788 | 11/1989 | Day et al. | 514/57 |
| 4,895,723 | 1/1990 | Amer et al. | 424/79 |
| 4,900,573 | 2/1990 | Meyers et al. | 426/302 |
| 4,923,981 | 5/1990 | Weibel et al. | 536/56 |
| 4,931,280 | 6/1990 | Wood et al. | 424/439 |
| 4,950,140 | 8/1990 | Pflavmer et al. | 514/23 |
| 4,996,063 | 2/1991 | Inglett | 426/21 |
| 5,015,477 | 5/1991 | Wood et al. | 424/439 |
| 5,019,399 | 5/1991 | Appelgren et al. | 424/440 |

FOREIGN PATENT DOCUMENTS

| | | |
|---|---|---|
| 0009858A1 | 4/1980 | European Pat. Off. . |
| 0119479A2 | 9/1984 | European Pat. Off. . |
| 0309029A1 | 3/1989 | European Pat. Off. . |
| 0323666A1 | 7/1989 | European Pat. Off. . |
| 0362926A1 | 4/1990 | European Pat. Off. . |

OTHER PUBLICATIONS

Renko et al., "A Study of Vascular Lesions Induced by Cholesterol Feeding and Methylcellulose Administration in Rabbits", *Cor Vasa*, 12(1), 65–74(1970).

Nightingale, "Lipid Binding From Aqueous Solution by Lipid Conjugated Hydroxypropyl Methylcellulose (HPMC)", a dissertation submitted to the University of Washington (1988), Obtained from the University of Washington Library.

Superko et al., "Effects of Solid and Liquid Guar Gum on Plasma Cholesterol and Triglyceride Concentrations in Moderate Hypercholesterolemia", *American Journal of Cardiology*, 51–55, Jul. 1, 1988.

Jenkins et al., "Dietary Fibres, Fibre Analogues, and Glucose Tolerance Importance of Viscosity", British Medical Journal, V. 1, No. 6124, 1392–1394, May 27, 1978.

Anderson et al., "Dietary Fiber and Coronary Heart Disease", *CRC Critical Reviews in Food Science and Nutrition*, V. 29, No. 2, pp. 95–147 (1990).

(List continued on next page.)

Primary Examiner—Ronald W. Griffin

[57] ABSTRACT

The present invention is directed to a baked food composition comprising food ingredients and a water-soluble cellulose ether which is useful for reducing the low-density lipoprotein serum cholesterol level of an animal. Use of a specific particle-size distribution of the water-soluble cellulose ether results in compositions which are more palatable than known compositions.

7 Claims, No Drawings

OTHER PUBLICATIONS

Council on Scientific Affairs, "Dietary Fiber and Health", *Journal of American Medical Association*, V. 262, No. 4,542-546, Jul. 28, 1989.

Warnick et al., "Dextran Sulfate-$Mg^{2+}$ Precipitation Procedure for Quantitation of High-Density-Lipoprotein Cholesterol", *Clinical Chemistry*, V. 28, No. 6, 1379-1388 (1982).

Reppas et al., "Effect of Hydroxypropylmethylcellulose on Gastrointestinal Transit and Luminal Viscosity in Dogs", *Gastroenterology*, V. 100, No. 5, 1217-1223 (1991).

Kritchevsky et al., "Influence of Dietary Fiber on Cholesterol Metabolism in Experimental Animals", *CRC Handbook of Dietary Fiber in Human Nutrition*, Chpt. 4.3, 129-142 (1986).

Anderson et al., "Dietary Fiber: Hyperlipidemia, Hypertension, and Coronary Heart Disease", *American Journal of Gastroenterology*, V. 81, No. 10, 907-919 (1986).

Gallaher et al., "The Effect of Dietary Fiber Type on Glycated Hemoglobin and Renal Hypertrophy in the Adult Diabetic Rat", *Nutrition Research*, V. 10, 1311-1323 (1990).

Noller, *Chemistry of Organic Compounds* (2nd Ed.), 404-405, W. B. Saunders Company (1957).

Lee et al., "Cholesterol-Lowering by Hydroxypropyl Methylcellulose and Guar Gum With Different Viscosities", *Fed. Am. Soc. Exp. Biol. J.*, Abst. #4127, V. 5, No. 5, A1082, Apr. 21-25, 1991.

Kirk-Othmer Concise Encyclopedia of Chemical Technology, 231-232, M. Grayson (ed), Wiley-Interscience, New York, N.Y. (1985).

*Chemical Abstracts*, V. 75, No. 3,234, Jul. 19, 1971, Abst. No. 17623b, S. Benko et al., "Vascular Lesions Induced by Cholesterol Feeding and Methyl Cellulose Administration in Rabbits".

Allain et al., "Enzymatic Determination of Total Serum Cholesterol", *Clincial Chemistry*, V. 20, 470 (1974).

*Chemical Abstracts*, V. 72, No. 21, 236-237, May 1970, Abstract No. 109611n, Benko et al., "Effect of Cholesterol Feeding and Methyl Cellulose Administration on the Total Lipid and Total Cholesterol Content in the Serum and Tissues".

*Chemical Abstracts*, V. 89, No. 7,485, Aug. 14, 1978, Abstract No. 58752A, K. Tsuji et al., "Effects of Polysaccharides on Cholesterol Metabolism. VII Effects of Various Polysaccharide . . . ".

Munoz et al., *American Journal of Clinical Nutrition*, vol. 32, pp. 580-592, Mar. 1979.

Topping et al., *British Journal of Nutrition*, (1988), 59, pp. 21-30.

EFFECT OF PARTICLE-SIZE DISTRIBUTION OF CELLULOSE ETHERS ON PALATABILITY OF COMPOSITIONS

BACKGROUND OF THE INVENTION

The field of this invention is achievement of improved palatability of compositions containing high-viscosity cellulose ethers of a specific particle-size distribution and the use of such compositions for reducing the serum cholesterol level of an animal.

The use of cellulose ethers in edible compositions and, in particular, pharmaceutical products, is well known. A common function of the cellulose ether in such uses is to serve as a controlled release agent. Typically, only minimal quantities, representing only a small percentage of a total formulation, of the cellulose ether are required in such uses.

A variety of compounds are currently known to be useful in reducing serum cholesterol levels in humans. However, many of these compounds, including both systemic and non-systemic compounds, have undesirable side effects or have certain characteristics that lead to difficulties in patients complying with their use. For example, characteristics such as the sandiness, grittiness, throat irritation, dispersion difficulties and phase separation of known compounds leads to very poor patient compliance. Accordingly, the search for new non-systemic compounds useful in reducing serum cholesterol levels in humans continues to be an important field of research.

Cholestyramine is an important, non-systemic compound known to be effective in treating high blood cholesterol levels, also known as hypercholesterolemia, which are believed to be responsible in many cases for arteriosclerosis in humans. Cholestyramine, which is typically orally consumed in order to effect its cholesterol lowering or controlling properties, is astringent and unpleasant to swallow. The cholestyramine also has the side effect of inducing constipation. Processes and compositions including cholestyramine are known, such as those described in U.S. Pat. Nos. 3,308,020; 3,383,281; 3,499,960; and 3,947,272.

It is known that soluble vegetable fibers such as psyllium, guar, and $\beta$-glucans may exert cholesterol lowering effects, but these soluble fibers are not very efficacious on a per gram basis. Also, because soluble vegetable fibers are easily metabolized by colonic bacteria (causing extensive anaerobic production of methane, carbon dioxide, and hydrogen), these vegetable fibers are known to cause gross flatulence, bloating and grave abdominal discomfort when administered in therapeutically effective doses. Furthermore, psyllium seed husk is typically contaminated with proteinaceous hull which carries the allergens known to be associated with psyllium.

Ground psyllium seed is recognized for its ability to lower serum cholesterol levels in human patients. EP-A-0362926 describes the use of products containing psyllium seed husk to be effective in reducing human serum cholesterol levels and in controlling blood glucose levels in diabetics.

EP-A-0309029 describes cookies containing psyllium and polyol polyesters which are useful in reducing blood cholesterol levels.

EP-A-0323666 describes the use of products containing cholestyramine in combination with psyllium or with polyol polyesters as orally administered cholesterol-lowering compositions.

Evidence of the unpalatability of compositions currently being marketed to treat hypercholesterolemia is the low rate of compliance by human patients to adhere to diets requiring daily consumption of these compositions. This low compliance rate indicates a definite need for a hypocholesteremia-controlling composition which is more palatable and more effective than the known compositions.

The present invention solves some of the above problems by disclosing a composition which is useful in a method for reducing serum cholesterol levels in human patients. Such compositions are more palatable and more effective than known compositions.

SUMMARY OF THE INVENTION

The present invention is directed to a bakable food composition comprising a mixture comprising, based on the total weight of the food composition:
a. from about 75 to about 98 weight percent of food ingredients other than the water-soluble cellulose ether of part (b); and
b. from about 2 to about 25 weight percent of a water-soluble cellulose ether which:
   i. has, as a 2 weight percent aqueous solution at 20° C., a viscosity of from about 10,000 mPa.s to about 2,000,000 mPa.s; and
   ii. has a particle size distribution, as measured prior to mixture with the other food ingredients, wherein at least about 40 weight percent of the water-soluble cellulose ether has a particle size from about 0.0006 meters to about 0.00025 meters, at least about 65 weight percent of the water-soluble cellulose ether has a particle size from about 0.0006 meters to about 0.00018 meters, and at least about 95 weight percent of the water-soluble cellulose ether has a particle size less than about 0.001 meters.

The present invention is also directed to a method of using the composition of this invention for the reduction of the serum cholesterol level of an animal comprising orally administering to said animal the composition in an amount on a daily basis effective to reduce the serum cholesterol level of the animal to a desired level.

DETAILED DESCRIPTION OF THE INVENTION

The composition of the present invention is useful for the treatment of high blood cholesterol levels, or hypocholesteremia, in animals and is more palatable than currently available compositions.

As used herein, the terms "palatable" and "palatability" are intended to refer to the taste and mouthfeel of the composition of the present invention upon being orally consumed by an animal. It is to be appreciated by those skilled in the art that these palatability characteristics are generally subjective and will typically vary from patient to patient that use the composition of the present invention. Different characteristics which may be used to describe the palatability of a composition include the sandiness, sliminess, grittiness, throat irritation, dispersion difficulties, and phase separation of the composition when orally consumed by an animal.

As used herein, the term "bakable food composition" is meant to refer to a food composition that may be or has been treated by a heat source in order to achieve a desired final food product. As such, the term "bakable food compositiion" includes both dough-type formulations and the baked or final product for consumption achievable from such dough-type formulations. Typically, such a bakable food composition will first be prepared as a dough or batter and then subjected to an elevated temperature in order to produce the desired product. Such baked food compositions will be edible and ingestible by the animal to whom such composition is provided.

Examples of baked food compositions are well known and include those such as cookies, cakes, biscuits, pies, crackers, wafers, muffins, granola bars, and bread. A preferred composition comprises a dosage amount of water-soluble cellulose ether in a cookie form. The water-soluble cellulose ether may be incorporated in the dough at levels from about 1 to about 10 g per cookie. Such a solid dosage form would preferably be ingested along with an appropriate amount of a liquid to assure adequate moisture availability for hydration of the water-soluble cellulose ether in the upper digestive tract of the animal. Typically, about 200 to about 500 ml of liquid is to be consumed.

The present invention provides an effective method for incorporation of a water-soluble cellulose ether into a cookie composition. Most conventional cookie recipes are useful in the present invention, provided the specific procedure described herein for incorporation of water-soluble cellulose ether is followed. Especially preferred is a molasses cookie composition.

The cookies of the present invention also comprise conventional cookie ingredients including, sugar, flour, shortening, egg and other conventional additives.

As used herein, the term "food ingredients other than the water-soluble cellulose ether" is meant to refer to those food ingredients, other than the water-soluble cellulose ethers described herein, which typically are used to prepare a desired baked food composition. As will be appreciated by one skilled in the art, a very wide variety of food ingredients may be used to prepare such a baked food composition.

Ordinary granulated sugars are satisfactory for use in making the cookies of the present invention. These include sucrose, dextrose, maltose, fructose, brown and invert sugars, alone or in combination. The preferred sugars are brown sugar and granulated sucrose. Corn syrups or molasses may also be used as the sugar component of the present invention however, the liquid component must be adjusted to compensate for the water in the syrup. Powder sugars can also be used. The amount of sugar useful in the compositions of the present invention is at conventional cookie composition levels, generally from about 20 percent to about 50 percent, preferably from about 25 percent to about 40 percent by weight of the cookie dough.

In the cookies described herein, the water-soluble cellulose ether cannot be used to simply substitute for the entire flour or starch component conventionally used in cookie compositions. If this were done, the result would be a crumbly cookie that would not stay in one piece. Thus, the cookies of the present composition are generally made with water-soluble cellulose ether and a reduced level of flour.

The flour for use in making the cookies of the present invention may be any finely comminuted meal of any cereal grain or edible seed, or mixtures thereof, as are known by one skilled in the art of baking. Typical non-limiting examples include wheat flour, barley flour, rye flour, cornstarch and corn flour, triticale, and also the so-called synthetic flours, which incorporate such materials as starch and soy protein isolate, with or without heat and/or steam treatment. The wheat flours are most typically employed in baking. They consist of several types including hard red spring, hard red winter, soft red winter and white winter and spring. These flour types are distinguished by differences in gluten quality, water absorption and protein content. Protein in these flours can vary from about 7 percent to about 14 percent, with the soft wheat flours having protein contents at the lower end of that range and the hard winter wheat flours having protein contents at the upper end of that range. Preferably, the flour used is a general-purpose wheat flour. The cookie dough of the present invention typically comprises about 4 percent to about 25 percent, preferably from about 5 percent to about 20 percent flour.

A starch source may be substituted for all or part of the flour. The starch can be any of the common food starches, for example, potato starch, corn starch, wheat starch, rice starch, barley starch, oat starch, tapioca starch, arrowroot, and sago starch. Modified starches can also be used. Preferably, the starch is pregelatinized, which helps to hold the baked cookie together, particularly at a reduced level of flour. Preferably, starch is substituted for from about 10 percent to about 50 percent of the flour component, thus comprising from about 1 percent to about 5 percent of the cookie dough composition.

The shortenings that can be employed in making the cookies of the present invention are well-known to those skilled in the art of baking and include solid or plastic, as well as liquid or semi-fluid, glyceride shortenings derived from animal, vegetable fats and oils including synthetically prepare shortenings. These glycerides can contain saturated or unsaturated "long-chain" acyl radicals having from about 12 to about 22 carbon atoms such as laurcyl, lauroyleoyl, myristoyl, myristoleoyl, palmitoy, palmitoleoyl, stearoyl, oleoyl, linoleoyl, linolenoyl, arachidoyl, arachidonoyl, behenoyl, erucoyl, and the like and are generally obtained from edible oils and fats such as corn oil, cottonseed oils, soybean oil, coconut oil, rapeseed oil, peanut oil, olive oil, palm oil, palm kernel oil, sunflower seed oil, safflower oil, lard, and tallow.

Some preferred shortenings are butter, soybean-based shortenings or oils, hydrogenated soybean-based shortening or oil, corn oil, palm oil, hydrogenated palm oil, lard and tallow oils. It is preferred that the shortening used in the present invention be in fluid form, i.e., liquid at room temperature or melted, when added to the other ingredients. From about 10 percent to about 35 percent, preferably from about 15 percent to about 32 percent by weight of the cookie dough comprises shortening.

Preferably, the shortening will contain an emulsifier which comprises from about 3 percent to about 30 percent of the shortening system. Suitable emulsifiers are lactylated mono- and diglycerides, propylene glycol monoesters, polyglycerol esters, sorbitan esters, diacetylated tartaric acid esters of mono- and diglycerides, citric acid esters of monoglycerides, stearoyl-2-lactylates, polysorbates, succinylated monoglycerides, acetylated monoglycerides, ethoxylated monoglycerides, lecithin, sucrose monoester, and mixtures thereof. Polyglycerol esters suitable for use in the present invention have an average of from about 2 to about 10 glycerol units and from 1 to 3 fatty acryl groups containing from about 14 to about 18 carbon atoms per glycerol moiety.

Although eggs, or a suitable protein substitute, are not a critical ingredient of the cookies of the present invention, eggs are preferably included to impart flavor, richness and color to the cookies. Fresh whole eggs are preferred for making the cookies of the present invention. Alternatively, egg solids, particularly egg albumen and dried yolk, may be used in baking the products disclosed herein. Soy isolates, whey protein concentrates, or other egg substitutes may also be used herein in combination with, or in place of, the egg solids. Such substitutes are well-known to those skilled in the art of baking. From about zero percent to about 15 percent by weight of the cookie dough, can comprise egg or egg substitute. When fresh whole egg is used, levels at the high end of this range are appropriate, whereas when dried egg solids are used lower levels are generally used.

The cookie dough of the present invention, as with conventional cookie dough, requires a liquid component. From about 3 percent to about 15 percent by weight of the dough, comprises the liquid component added either via fresh egg (e.g., egg yolk, egg white, or whole egg), water, or a fresh egg plus water mixture. When fresh egg is used as the liquid component, it is generally included at from about 10 percent to about 15 percent of the dough. When water is utilized as the liquid component it is generally included at from about 10 percent to about 15 percent of the dough. When water is utilized as the liquid component it is generally included at from about 3 percent to about 5 percent of the dough.

The "conventional additives" useful in making the cookies of the present invention include ingredients such as leavening agents, flavors, and flavor additives, colors, nutrients, antioxidants, and antimicrobial agents.

The chemical leavening agents can comprise a baking soda, e.g., sodium, potassium, or ammonium bicarbonate, and/or a baking acid, preferably sodium aluminum phosphate, monocalcium phosphate, dicalcium phosphate or mixtures thereof. The selection of the leavening system is within the knowledge of one skilled in the art. Form zero percent to about 2 percent, preferably from about 0.1 percent to about 2 percent of the cookie dough of the present invention will typically be leavening agent.

The flavor additives can be of a type that remain as whole pieces in the cookie. Such additives include, but are not limited to, chocolate, peanut butter or butterscotch chips or chunks, fruit or fruit-flavored bits, such as blueberry, strawberry, or citrus flavored bits, or other fruit flavored bits, such as cherry, blackberry, apricot, raisin, date, or apple. Cereals may also be used, such as bran or oatmeal, as may nutmeats including the whole or chopped meat of any edible nut including walnuts, black walnuts, hickory nuts, hazel nuts, brazil nuts, peanuts, macadamia nuts, pecans, almonds, cashews, coconut and the like. From zero percent to about 30 percent of the cookie dough can be such additives.

Other flavor additives may be incorporated into the cookie dough prior to baking to add flavor, aroma and color to the final baked cookie. Examples include spices, such as cinnamon, mace, nutmeg, caraway, anise, allspice, poppy seed, coriander, ginger, cloves, fennel, and salt; and flavorings, such as banana, orange, lemon, mint or vanilla, at levels up to about 10 percent of the cookie dough. Honey or molasses may also be used in the present invention at levels up to about 15 percent. Mixtures of these flavorings and whole piece components can be added to provide a variety of desirable products. The cookies of the present invention are well-suited to compositions with high oil contents. The exact amount added for any of these flavoring components (whether they are of the type that is blended into the composition or the type that remain as whole pieces) will depend on personal preference and on what particularly is being added.

Preferred cookies of the present invention comprise:
(a) from about 5 percent to about 20 percent of water-soluble cellulose ether;
(b) from about 10 percent to about 35 percent of a shortening component;
(c) from about 15 percent to about 50 percent of a sugar component;
(d) from about zero percent to about 30 percent of a flour component;
(e) from about zero percent to about 30 percent of a starch component;
(f) from about zero percent to about 15 percent of an egg component;
(g) the remainder being conventional cookie additives.

Cellulose ethers have long been used in many industries as, for example, viscosity control agents, emulsifiers, and binding agents. The use of cellulose ethers in pharmaceutical products is also well known. The usual function of cellulose ethers in pharmaceutical products is to serve as a coating, compounding aid, or controlled release agent.

The water-soluble cellulose ethers used in the present invention may be prepared by any of a number of known methods described, for example, in U.S. Pat. Nos. 3,342,805, 3,388,082, 3,709,876, 4,477,657, 4,410,693, and 4,820,813.

Generally, a specific cellulose ether is prepared by the formation of an alkali cellulose by the addition of sodium hydroxide to a slurry of cellulose floc in a diluent. The alkali cellulose is then reacted with an appropriate alkylating agent or agents, under pressure. Thereafter, the slurry is neutralized and the product is extracted, dried, and ground.

The cellulose ethers employed in the present invention must be water-soluble. As used herein, the term "water-soluble" means that two grams of a powdered cellulose ether of the present invention can be dispersed by stirring into 100 grams of water at a temperature between about 0° C. and 100° C., to provide a substantially clear solution or dispersion (gel) when the dispersion is brought to a temperature of 20° C.

Examples of water-soluble cellulose ethers useful in the present invention include such known water-soluble cellulose ethers as methylcellulose, methylethylcellulose, hydroxypropyl methylcellulose, hydroxypropyl cellulose, and hydroxyethyl methylcellulose. Mixtures of such known water-soluble cellulose ethers may also be used in the present invention. The most preferred water-soluble cellulose ethers for use in the present invention are methylcellulose and hydroxypropyl methylcellulose.

Particularly preferred water-soluble cellulose ethers for use in the present invention include (with all weight percents based on the total weight of the water-soluble cellulose ether): a methylcellulose with a methoxyl substitution of between about 27.5 to about 31.5 weight percent; a hydroxypropyl methylcellulose with a methoxyl substitution of between about 19 to about 24 weight percent and a hydroxypropoxyl substitution of between about 4 to about 12 weight percent; and a hydroxypropyl methylcellulose with a methoxyl substitution of between about 27 to about 30 weight percent and a hydroxypropoxyl substitution of between about 4 to about 7.5 weight percent; and a hydroxypropyl methylcellulose with a methoxyl substitution of between about 28 to about 30 weight percent and a hydroxypropoxyl substitution of between about 7.5 to about 12 weight percent.

Descriptions of suitable water-soluble cellulose ethers, which meet the criteria of the present invention as described herein, can be found in the following references: alkyl and hydroxyalkylalkylcellulose (Chapter 3), hydroxyethylcellulose (Chapter 12), and hydroxypropylcellulose (Chapter 13) in *Handbook of Water-Soluble Gums and Resins*, ed. R. L. Davidson, pub. McGraw-Hill (1980); and hydroxypropyl methylcellulose (pp 670-71) and methylcellulose (pp 864-865) in *The United States Pharmacopeia*, (The National Formulary), (USP XXII, 1990).

The water-soluble cellulose ethers of the present invention are inert, non-ionic cellulose ethers which are known to be edible. The use of such water-soluble cellulose ethers in an edible composition is characterized in that the water-soluble cellulose ethers:

1. are resistant to bacterial fermentation in the lower bowel of the animal and, therefore, avoid gas production resulting from such fermentation,
2. are substantially unaffected by human or bacterial enzymes found in the gut,
3. do not cross the gut wall,
4. do not enter the circulatory system,
5. do not produce the allergic responses characteristic of many known vegetable fibers, and
6. minimally affect micronutrient absorption.

The particular cellulose ethers which are useful in the present invention are those which are of a high-viscosity grade. By "high-viscosity grade" is meant those cellulose ethers that exhibit a calculated viscosity of at least about 10,000 mPa.s and may have a viscosity as high as about 2,000,000 mPa.s. Such viscosities may typically be measured by conventional methods wherein, for example, a 2 weight percent aqueous solution of the cellulose ether at 20° C. is measured using Ubbelohde capillary tubes. Unless otherwise indicated, all cellulose ether viscosities specified herein represent a calculated viscosity for the cellulose ether when as a 2 weight percent aqueous solution at 20° C.

Preferably, the cellulose ethers useful in the present invention exhibit a viscosity ranging from about 25,000 mPa.s to about 800,000 mPa.s. Most preferably, the cellulose ethers exhibit a viscosity ranging from about 50,000 mPa.s to about 600,000 mPa.s.

In certain advantageous embodiments of the invention, water-soluble, high viscosity cellulose ethers having a viscosity greater than about 100,000 mPa.s may be prepared, for example, by a process taught in U.S. Pat. No. 4,820,813, wherein a substantially dry high molecular weight cellulose ether is ground under conditions of mild mechanical impact such as those encountered in a high speed air swept impact mill.

Conversely, as used herein, "low-viscosity grade" is meant those cellulose ethers that exhibit a viscosity less than about 10,000 mPa.s.

The high-viscosity grade, water-soluble cellulose ethers of the present invention are further characterized in that they are generally palatable to patients and may be easily incorporated into a composition which will be palatably acceptable to patients.

Generally, in order to achieve a substantially equivalent cholesterol reduction, a larger amount of a lower viscosity grade water-soluble cellulose ether will typically need to be used as compared to a higher viscosity grade water-soluble cellulose ether. Also, it will be typically preferred to use as little of the water-soluble cellulose ether as possible while still achieving the desired results. As such, it is preferred that a higher viscosity grade of a water-soluble cellulose ether be used in the present invention.

As used herein, the term "workable" is intended to refer to the ability to handle and process a composition comprising a water-soluble cellulose ether of the present invention and other food ingredients in order to easily achieve a desired final product. As will be appreciated by one skilled in the art, the workability of a specific composition of the present invention will depend on the specific materials comprising the composition as well as the process and conditions used to prepare a desired final composition.

In preparing the compositions of the present invention, it is preferable that the water-soluble cellulose ether not be allowed to hydrate during the preparation of the composition. Such hydration of the water-soluble cellulose ether will typically adversely affect the workability of the composition. As such, it will typically be preferable to add the water-soluble cellulose ether after substantially all of the other food ingredients have been mixed together.

The water-soluble cellulose ether should be used in an amount effective to provide a composition with a desired palatability and workability. Typically, the water-soluble cellulose ether will be present in the composition of the present invention, based on the total weight of the composition, from about 2 to about 30 weight percent. Preferably, the water-soluble cellulose ether will be present in the composition of the present invention from about 5 to about 20 weight percent. Most preferably, the water-soluble cellulose ether will be present in the composition of the present invention from about 10 to about 20 weight percent.

It has been surprisingly discovered that the use of a specific particle-size distribution of the water-soluble cellulose ether of the present invention results in a composition having an unexpectedly superior palatability as compared to the use of the same water-soluble cellulose ether without the specific particle-size distribution.

The required particle size distribution of the water-soluble cellulose ether, as measured prior to mixture with the other food ingredients, is wherein at least about 40 weight percent of the water-soluble cellulose ether has a particle size from about 0.0006 meters to about 0.00025 meters, at least about 65 weight percent of the water-soluble cellulose ether has a particle size from about 0.0006 meters to about 0.00018 meters, and at least about 95 weight percent of the water-soluble cellulose ether has a particle size less than about 0.001 meters.

Preferably, the particle size distribution of the water-soluble cellulose ether, as measured prior to mixture with the other food ingredients, is wherein at least about 50 weight percent of the water-soluble cellulose ether has a particle size from about 0.0006 meters to about 0.00025 meters, at least about 80 weight percent of the water-soluble cellulose ether has a particle size from about 0.0006 meters to about 0.00018 meters, and at least about 95 weight percent of the water-soluble cellulose ether has a particle size less than about 0.001 meters.

Most preferably, the particle size distribution of the water-soluble cellulose ether, as measured prior to mixture with the other food ingredients, is wherein at least about 75 weight percent of the water-soluble cellulose ether has a particle size from about 0.0006 meters to about 0.00025 meters, at least about 90 weight percent of the water-soluble cellulose ether has a particle size from about 0.0006 meters to about 0.00018 meters, and at least about 95 weight percent of the water-soluble cellulose ether has a particle size less than about 0.001 meters.

In order to obtain a desired particle size distribution, a crude water-soluble cellulose ether having an unacceptable particle size distribution may be seived and the necessary cuts retained for use in the present invention. Alternatively, a water-soluble cellulose ether having a too small particle size distribution may be agglomerated by known methods before being seived to obtain the desired particle size distribution.

It has been found that a water-soluble cellulose ether having too small of a particle size adversely affects the palatability of the composition of the present invention. While not wishing to be held to any one particular theory, it is believed that a water-soluble cellulose ether having too small of a particle size has so much surface area that it is rapidly hydrated by saliva in the mouth.

It has also been found that a water-soluble cellulose ether having too large of a particle size adversely affects the palatability of the composition of the present invention. While not wishing to be held to any one particular theory, it is believed that a water-soluble cellulose ether having too large of a particle size leads to unpleasant graininess or grittiness in the mouth.

Preferably, the water-soluble cellulose ether used in the present invention should not have a bulk density that is too great. Preferably, the water-soluble cellulose ether has a bulk density that is less than about 0.5 g/cm$^3$. The use of a water-soluble cellulose ether that has a bulk density that is too large may result in a composition that is not very palatable due to the grittiness of such particles.

Method of Making

Incorporating a water-soluble cellulose ether into a cookie involves more than just mixing the desired amount of water-soluble cellulose ether into a conventional cookie composition. If a water-soluble cellulose ether is added this way, the water-soluble cellulose ether will hydrate and result in a less palatable cookie. The present invention provides a method for incorporating the water-soluble cellulose ether in a way that avoids hydration of the water-soluble cellulose ether during the mixing, forming and baking of the cookie, thereby forming an esthetically-appealing, more palatable water-soluble cellulose ether-containing cookie.

The method of the present invention for making a water-soluble cellulose ether-containing cookie comprises tieing-up the water in the cookie dough system with part or all of the dry ingredient components in the dough, prior to mixing in the other cookie dough ingredients, particularly the water-soluble cellulose ether. Mixing the dough in this way reduces the water availability in the cookie dough, thereby inhibiting hydration of the water-soluble cellulose ether during the mixing and baking process. The dry ingredients which may be used to serve this function include sugar, flour, non-pre-gelatinized starch, egg solids, protein solids or mixtures thereof. All or part of these dry ingredients in the cookie may be used for this purpose. Those dry ingredients, or portions thereof, which are not used to tie-up the water may be added to the cookie dough at a later point in the mixing process.

The method of the present invention comprises a premixing step during which the liquid components of the dough (i.e., water, fresh egg or water plus fresh egg mixture) are mixed with a dry ingredient component selected from sugar, flour, non-pre-gelatinized starch, egg solids, protein solids, or mixtures thereof. It is preferred that the dry ingredients used in the premix step be selected from sugar, flour or mixtures thereof.

Preferably, the dry ingredient component that is premixed with the liquid component comprises part or all of the sugar used in the cookie dough. The sugar used in the pre-mix step comprises from about 10 percent to about 30 percent by weight of the dough. Utilization of the sugar in this pre-mixing step assures distribution of all of the cookie ingredients in the dough and additionally makes the dough easier to handle and form. Most preferably, the dry ingredient component is sucrose. As an alternative to actually mixing sugar with water in the premix step, it is possbile to utilize a preformed mixture of sugar and liquid, as would be the case with honey or corn syrup. The use of these pre-formed mixtures is intended to fall within the present invention. Pre-gelatinized starch should not be included in the dry ingredient component of the premix (although it may be included in later stages of the mixing) because it ties up the liquid component too tightly resulting in a less acceptable cookie.

The liquid component in the pre-mixing step comprises from about 3 percent to about 15 percent by weight of the dough. As described above, the liquid component of the cookie dough may comprise water, fresh egg, or a mixture of water and fresh egg. The dry ingredient component in the pre-mixing step comprises from about 0.6 percent to about 35 percent by weight of the dough.

The premixture is then combined with a fluid shortening component, as described hereinbefore, in such an amount that the shortening component comprises from about 10 percent to about 35 percent by weight of the final cookie dough. If the shortening is not already in fluid form, it should be melted or softened before it is combined with the premix. The inclusion of the shortening at this point in the process allows the cookie dough to be easily worked in conventional mixing equipment. Preferably the shortening comprises butter or a hydrogenated soybean-based shortening.

The pre-mix/shortening mixture may then be combined with the other conventional cookie components to provide the cookie dough of the present invention.

To provide a dough which has even distribution of components and which is particularly easy to handle and form, the water-soluble cellulose ether is added last.

The cookie ingredients can be mixed using any conventional batch cookie mixing equipment, for example a Hobart mixer.

Mixing the cookie ingredients in this way minimizes hydration of the water-soluble cellulose ether in the mixing process. Combining the specified dry ingredients, especially sugar, with the liquid component, especially water, before combining with the water-soluble cellulose ether minimizes the water availability so that the water does not hydrate the water-soluble cellulose ether when the cookie ingredients are mixed. This enables the creation of a water-soluble cellulose ether-containing cookie which has a texture similar to that of a conventional cookie. Furthermore, mixing the ingredients in this way slows undesirable hydration of the water-soluble cellulose ether in the mouth upon eating. Thus, the cookies made by this method have taste and mouthfeel similar to conventional cookies.

A preferred method of making the cookie of the present invention includes the following steps:

(a) combining from about 3 percent to about 15 percent by weight of the dough, of a liquid component selected from the group consisting of water, fresh egg, and mixtures thereof, with from about 10 percent to about 30 percent by weight of the dough, of a sugar component;

(b) combining from about 10 percent to about 35 percent by weight of the dough, of a fluid shortening component with the mixture of (a);

(c) mixing together from about zero percent to about 30 percent, by weight of the dough, of a flour component from about zero percent to about 30 percent, by weight of the dough, of a starch component from about 0.1 percent to about 2 percent, by weight of the dough, of a dry egg white component, and then combining this mixture with the mixture of (b).

(d) mixing from about 5 percent to about 30 percent, by weight of the dough, of a water-soluble cellulose ether component with the mixture of (c).

From about 10 g to about 40 g portions of the cookie dough prepared by the present method are placed evenly spaced on a conventional baking sheet and baked using radiant, conductive or convective exposure to energy of a type which imparts thermal energy to the product being baked, such as conventional, convection, microwave or combinations thereof. Baking times and temperatures are dependent, on the type of oven use. Generally, the cookies are baked at temperatures from about 300° F. (149° C.) to about 375° F. (190° C.) for from about 5 minutes to about 15 minutes.

The cellulose ethers of the present invention are further characterized in that they are generally palatable to animals and/or can be easily incorporated into a composition which can be made to be palatably acceptable to an animal, particularly a human patient.

For the purposes of the present invention, the term "animal" means a warm-blooded mammal, especially a human.

In the present specification and claims, the terms "amount effective" and "effective amount" represent the minimum amount of the compounds of the present invention, or mixtures thereof, which is necessary to prepare the desired composition of the present invention as well as the minimum amount of the composition of the present invention which is necessary to achieve a desired reduction of the blood cholesterol level of an animal. The amount of the compositions of the present invention to be administered to an animal will be dictated by such considerations as the desired blood cholesterol level to be achieved, cost, palatability, physical side effects, potential patent non-compliance, and incompatibility of the compositions with other components of the animal's diet.

Due to the above-identified considerations, the water-soluble cellulose ether of the present invention will generally be used in daily consumption in an amount from at least about 5 grams, preferably ranging from about 10 grams to about 50 grams, per day for an individual animal. This may be accomplished, for example, by a daily ingestion of from about 2 to about 4, preferably about 3, cookies each containing from about 2 gram to about 10 grams of water-soluble cellulose ether at two or three regularly spaced intervals throughout the day. This treatment regimen may be continued until the animal's condition is relieved.

The water-soluble cellulose ethers which are useful in the present invention are those cellulose ethers which reduce the low-density lipoprotein serum cholesterol level in a human patient. These particular cellulose ethers unexpectedly help to reduce a human patient's low-density lipoprotein serum cholesterol level when compared to the performance of other known products.

The compositions of the present invention are administered to an animal through regular oral administrations of said compositions so as to provide an effective amount of the water-soluble cellulose ether. The compositions may be administered in the present invention in a dry dosage form wherein the water-soluble cellulose ether will hydrate following oral ingestion by an animal.

The compositions of the present invention are intended to be administered to an animal in need of selective reduction of serum lipid levels, specifically total serum cholesterol, LDL cholesterol levels, and triglyceride levels.

In the present specification and claims, the term "pre-treatment low-density lipoprotein serum cholesterol level" or "pre-treatment LDL serum cholesterol level" is employed to designate the amount or level of low-density lipoprotein (LDL) serum cholesterol exhibited by an animal (or human patient) prior to treatment with the method of the present invention using a water-soluble, high-viscosity grade cellulose ether. Such a pre-treatment LDL serum cholesterol level will generally vary from patient to patient. Such a pre-treatment LDL serum cholesterol level for a human patient may generally be determined by known methods. The LDL serum cholesterol level for normal human patients range from about 75 to about 160 mg/dL, but values above about 130 mg/dL represent increasing risk of coronary heart disease.

The LDL serum cholesterol level is generally determined by $$C_{LDL} = C_{Total} - C_{HDL} - (\text{Triglycerides}/5)$$

wherein:
C=cholesterol in mg/dL;
LDL=low-density lipoprotein serum cholesterol; and
HDL=high-density lipoprotein serum cholesterol.

In the present specification and claims, the term "desired low-density lipoprotein serum cholesterol level" or "desired LDL serum cholesterol level" is employed to designate the amount or level of LDL serum cholesterol exhibited by an animal, particularly a human patient, desired after treatment with the method of the present invention using a water-soluble, high-viscosity grade cellulose ether. Such a desired LDL serum cholesterol level for a given human patient will generally be predetermined by a physician and will depend on the pre-treatment LDL serum cholesterol level. However, such a desired LDL serum cholesterol level will generally be dictated by specific characteristics and health requirements and, as such, will vary from patient to patient. Typically, the desired LDL serum cholesterol level for a human patient will range from about 75 to about 160 mg/dL but will preferably not exceed about 130 mg/dL.

In the present specification and claims, the term "post-treatment low-density lipoprotein serum cholesterol level" or "post-treatment LDL serum cholesterol level" is employed to designate the amount or level of LDL serum cholesterol exhibited by an animal, particularly a human patient, after treatment in accordance with the method of the present invention using a water-soluble, high-viscosity grade cellulose ether.

As used herein, the term "serum lipid levels" refers to total serum cholesterol, serum triglycerides, and LDL and HDL serum cholesterol levels. The term "reduction in serum lipid levels" does not include a reduction in HDL cholesterol level. Particularly, LDL serum cholesterol levels are selectively reduced, and frequently triglycerides are also reduced.

It has been discovered that by using the method of the present invention, the total serum cholesterol level for a human patient may be reduced from about at least 15 percent up to about 50 percent, based on the pre-treatment total serum cholesterol level.

It has also has been discovered that the method of the present invention provides a "selective" reduction of the concentration of circulating serum LDL. cholesterol in the patient's bloodstream. The term "selective" means that the circulating serum LDL cholesterol is reduced (usually in a clinically significant amount of at least about 15 percent from the pre-treatment level) without producing an alteration in the high-density lipoprotein serum cholesterol levels (HDL). Selective reduction of circulating serum LDL cholesterol up to 50 percent is achievable through treatment with the cellulose ethers of the present invention. In the same study discussed above, an average reduction in LDL cholesterol levels of 33 percent was observed after one week of treatment.

It has been discovered that use of the method of the present invention also results in clinically significant reductions of serum triglyceride levels.

It is generally recognized that those skilled in the medical and pharmaceutical arts do not currently understand the full mode of action of soluble dietary fibers in the process of cholesterol lowering. What is evident from the findings of this invention is that by providing the human body a generous supply of benign soluble dietary fiber in the form of a high-viscosity grade cellulose ether, natural human body processes are mobilized and assisted to achieve reductions in circulating LDL cholesterol levels via a non-systemic. non-invasive therapy, with concomitant likelihood of minimal unwanted systemic side effects.

The following examples illustrate the present invention and the manner by which it can be practiced but, as such, should not be construed as limitations upon the overall scope of the same. Unless otherwise indicated, all percentages and ratios are by weight.

EXAMPLES

Preparation of Standard Cookie Formulation

A standard molasses sugar cookie batter for the preparation of twenty cookies is prepared by first blending together to a uniform paste:

| one raw egg white and yolk | (55 g), |
| ¼ pound of unsalted butter | (115 g), |
| ¼ cup unsulphured molasses | (85 g), and |
| ¾ cup of granulated sugar | (155 g) | in a suitable mixing bowl.

To this paste is then added a sifted dry-powder blend of:

| 1 cup white general purpose flour | (165 g), |
| 2 teaspoons baking soda | (12.5 g), |
| ¾ teaspoon table salt | (4.0 g), |
| ½ teaspoon ground ginger | (2.0 g), |
| ¼ teaspoon ground cloves | (1.0 g), and |
| 1 teaspoon ground cinnamon | (2.5 g). |

The paste and dry-powder mixture is thoroughly blended to form an homogeneous cohesive batter weighing 600 g, or twenty portions, each of 30 g.

Each individual cookie for baking and palatability testing is formed by thoroughly blending and kneading together one 30 g portion of this standard batter with 5.0 g of a water-soluble cellulose ether, as described below, to form a cohesive dough-ball approximately 3 cm in diameter. Each dough ball is then rolled in granulated sugar to pick up a surface coating of sugar granules weighing about 0.7 g, then pressed onto an anti-stick baking pan to form a circular raw cookie approximately 5.5 cm in diameter and 1.2 cm in height.

Groups of ten raw cookies are then baked for 11 minutes at 325°±15° F. (163°±8° C.) to yield golden-brown colored circular cookies ranging in diameter from about 6.5 cm to 8 cm depending on the composition of the cellulose ether in the dough and the particle size distribution of that cellulose ether powder or granule.

COMPARATIVE EXAMPLE 1

Reference cookies for comparison palatability testing are prepared as described above except that 5 g of additional white flour is added to the cookie batter in lieu of a water-soluble cellulose ether powder.

The various cellulose ethers incorporated into the molasses sugar cookies are characterized as follows:

COMPARATIVE EXAMPLE 2

A methylcellulose powder is used, having a methoxyl content in the range of 27.5 to 31.5 percent by weight, and exhibiting a 2 percent aqueous viscosity at 20° C. of 4200 mPa.s. More than 95 percent of this methylcellulose powder passes through a sieve opening of 0.250 mm, and more than 85 percent passes through a sieve opening of 0.177 mm. This powder shows an apparent density of 0.35 g/cm³.

EXAMPLE 1

A methylcellulose powder is used having a methoxyl content in the range of 27.5 to 31.5 percent by weight, and exhibiting a 2 percent aqueous viscosity at 20° C. of 21,800 mPa.s. 1,300 Grams of this powder is converted to granular form by moistening it under high-intensity mixing conditions at 25° to 40° C. in a blender with 750 g of water to form a crumbly moist granulate, which is then tray-dried at 110° C. for six hours in a convection oven. This dry, friable granulate is then separated into a series of sieve cuts by passing the dry granulate downward through an agitated vertical stack of sieves of decreasing mesh sizes and collecting the granules retained on each sieve or in the bottom pan.

In this manner, this methylcellulose is obtained in granules having the following particle size characteristics:
(a) particles of sizes less than 1.00 mm but greater than 0.595 mm,
(b) particles of size less than 0.595 mm, but greater than 0.420 mm,
(c) particles of size less than 0.420 mm, but greater than 0.250 mm,
(d) particles of size less than 0.250 mm, but greater than 0.177 mm.
(e) particles of size less than 0.177 mm.

The apparent density of each of these granule sieve cuts is in the range 0.33 to 0.38 g/cm³.

COMPARATIVE EXAMPLE 3

A hydroxypropylmethylcellulose is used having a methoxyl content in the range of 28 to 30 percent by weight and a hydroxypropoxyl content in the range of 7 to 12 percent by weight, and exhibiting a 2 percent aqueous viscosity at 20° C. of 4800 mPa.s is used. This freely flowing granulate is separated into sieve cuts as described in Example 1. These granulate sieve cuts show apparent densities in the range of 0.33 to 0.45 g/cm³.

EXAMPLE 2

A hydroxypropylmethylcellulose is used having a methoxyl content in the range of 27 to 30 percent by weight and a hydroxypropoxyl content in the range of 4.0 to 7.5 percent by weight, and exhibiting a 2 percent aqueous viscosity at 20° C. of 317,000 m.Pas is used. This granulate is separated into the same mesh sizes as described in Example 1. Each of these granule mesh sizes shows an apparent density in the range of 0.20 to 0.30 g/cm³.

EXAMPLE 3

A hydroxypropylmethylcellulose is used having a methoxyl content in the range of 19 to 25 percent by weight and a hydroxypropoxyl content in the range of 4 to 12 percent by weight, and exhibiting a 2 percent aqueous viscosity at 20° C. of 27,300 mPa.s is used. This low density granule mixture is separated into mesh sizes as described in Example 1.

These granulate mesh cuts show apparent densities in the range of 0.12 to 0.25 g/cm³.

EXAMPLE 4

A hydroxypropylmethylcellulose is used having a methoxyl content in the range of 19 to 25 percent by weight and a hydroxypropoxyl content in the range of 4 to 12 percent by weight, and exhibiting a 2 percent aqueous viscosity at 20° C. of 68,600 mPa.s. This powder shows a particle size distribution like that given above for Comparative Example 2, and shows an apparent powder density of 0.42 g/cm³.

EXAMPLE 5

A hydroxypropylmethylcellulose granules is used having a methoxyl content in the range of 19 to 25 percent by weight and a hydroxypropoxyl content in the range of 4 to 12 percent by weight, and exhibiting a 2 percent aqueous viscosity at 20° C. of 104,000 mPa.s is obtained by moistening and drying powdered material in a fluidized bed granulator.

The dry granulate mixture is separated into mesh sizes as described in Example 1. These granulate mesh cuts show densities in the range of 0.2 to 0.4 g/cm³.

EXAMPLE 6

A hydroxypropylmethylcellulose is used having a methoxyl content in the range of 19 to 25 percent by weight and a hydroxypropoxyl content in the range of 4 to 12 percent by weight, and exhibiting a 2 percent aqueous viscosity at 20° C. of 400,000 mPa.s. This low-density granulate mixture is separated into mesh sizes as described in Example 1. Mesh size analysis shows the granule mixture contains less than 0.5 percent by weight of particles above range (a), 25 percent by weight within range (a), 32 percent by weight within range (b), 20 percent within range (c), 7 percent within range (d), and 18 percent in range (e). These granulate mesh cuts show apparent densities in the range of 0.12 to 0.33 g/cm³.

Palatability Testing

Portions of the various cookies, prepared as described in the Examples, are chewed up and evaluated for taste and texture palatability by a panel of human judges. The results of these evaluations are shown in Table 1. The cookies are especially evaluated for obvious graininess or grittiness in mouth texture on chewing, and for the onset of the strong slimy and tacky sensation in the mouth characteristic of particulate water-soluble cellulose ethers in bakable food compositions.

The unexpected and surprising result of these palatability tests is that when the water-soluble cellulose ether incorporated into a bakable good composition has a viscosity of at least about 10,000 mPa.s, the particle-size distribution plays a critical role in affecting the observed palatability of the bakable food composition.

In particular, if the particle-size distribution of the water-soluble cellulose ether incorporated into the bakable food composition lies predominantly in the range from about 0.00025 to about 0.0006 m, the characteristic tackiness and sliminess is not observed and a highly palatable bakable food composition is obtained, comparable in taste and texture to the control cookie containing no water-soluble cellulose ether.

When a significant fraction of the incorporated water-soluble cellulose ether is above about 0.0006 meter, the expected graininess, due to large particles, is readily detected. When a significant fraction of the incorporated water-soluble cellulose ether has a particle-size below about 0.00025 meter, tackiness and sliminess is observed when chewing the cookies.

TABLE I

Results of Taste and Texture Palatability Tests on Cookies Containing Cellulose Ethers Listed in the Examples in Various Particle Size Ranges and Particle Size Distributions. Incorporated at Approximately 15 Percent by Weight

| Cookie Formulation | 2 Percent Aqueous Viscosity of Cellulose Ether (mPa.s) | Particle Size Range of Cellulose Ether Incorporated at 5 g per 35 g Cookie | Results of Taste and Texture Palatability Testing. Comparison to Reference Cookie | | |
|---|---|---|---|---|---|
| | | | Comparison | Graininess Grittiness on Chewing | Tackiness Sliminess on Chewing |
| Comp. Ex. 1 | No cellulose ether present | Not Present | Reference | None | Very Slight |
| Comp. Ex. 2 | 4,200 | Unsieved | Comparable | No | Slight |
| Comp. Ex. 3 | 4,800 | (a) | Comparable | Slight | None |
| | | (b) | Equivalent | None | None |
| | | (c) | Equivalent | None | None |
| | | (d) | Equivalent | None | None |
| | | (e) | Equivalent | None | None |
| Example 1 | 21,800 | (a) | Inferior | Obvious | None |
| | | (b) | Equivalent | None | None |
| | | (c) | Equivalent | None | None |
| | | (d) | Comparable | None | Very Slight |
| | | (e) | Inferior | None | Moderate |
| Example 2 | 317,000 | (a) | Inferior | Obvious | None |
| | | (b) | Comparable | Slight | None |
| | | (c) | Comparable | Slight | None |
| | | (d) | Comparable | Slight | Very Slight |
| | | (e) | Inferior | None | Moderate |
| Example 3 | 27,300 | (a) | Inferior | Obvious | Slight |
| | | (b) | Comparable | None | Slight |
| | | (c) | Comparable | None | Slight |
| | | (d) | Inferior | None | Strong, Tacky |
| | | (e) | Inferior | None | Strong, Tacky |
| Example 4 | 68,600 | 85 percent less than .000180 m | Inferior | None | Very Slimey |
| Example 5 | 104,000 | (c) | Comparable | None | Very Slight |
| | | (d) | Inferior | None | Moderate |
| Example 6 | 400,000 | Unsieved | Comparable | None | Very Slight |
| | | (a) | Inferior | Moderate | None |
| | | (b) | Equivalent | None | None |
| | | (c) | Equivalent | None | None |
| | | (d) | Comparable | None | Very Slight |
| | | (e) | Inferior | None | Moderate |

(a) = .001000–.000595 m
(b) = .000595–.000420 m
(c) = .000420–.000250 m
(d) = .000250–.000180 m
(e) = Less than .000180 m

What is claimed is:

1. A bakable food composition comprising a mixture comprising, based on the total weight of the food composition:
   a. from about 75 to about 98 weight percent of food ingredients other than the water-soluble cellulose ether of part (b); and
   b. from about 2 to about 25 weight percent of a water-soluble cellulose ether which:
      i. has, as a 2 weight percent aqueous solution at 20° C., a viscosity of from about 10,000 mPa.s to about 2,000,000 mPa.s; and
      ii. has a particle size distribution, as measured prior to mixture with the other food ingredients, wherein at least about 40 weight percent of the water-soluble cellulose ether has a particle size from about 0.0006 meters to about 0.00025 meters, at least about 65 weight percent of the water-soluble cellulose ether has a particle size from about 0.0006 meters to about 0.00018 meters, and at least about 95 weight percent of the water-soluble cellulose ether has a particle size less than about 0.001 meters.

2. The composition of claim 1 wherein the water-soluble cellulose ether is methylcellulose or hydroxypropyl methylcellulose.

3. The composition of claim 1 wherein the water-soluble cellulose ether has a viscosity of from about 25,000 mPa.s to about 800,000 mPa.s.

4. The composition of claim 1 wherein the water-soluble cellulose ether has a viscosity of from about 50,000 mPa.s to about 600,000 mPa.s.

5. The composition of claim 1 wherein the food composition comprises a mixture comprising, based on the total food composition:
   a. from about 80 to about 95 weight percent of food ingredients other than the water-soluble cellulose ether of part (b); and
   b. from about 5 to about 20 weight percent of a water-soluble cellulose ether.

6. The composition of claim 5 wherein the food composition comprises a mixture comprising, based on the total food composition:
   a. from about 80 to about 90 weight percent of food ingredients other than the water-soluble cellulose ether of part (b); and
   b. from about 10 to about 20 weight percent of a water-soluble cellulose ether.

7. The composition of claim 1 wherein the food composition is a cookie comprising, based on the total food composition:
   a. from about 80 to about 90 weight percent of food ingredients other than the water-soluble cellulose ether of part (b); and
   b. from about 10 to about 20 weight percent of a hydroxypropyl methylcellulose with a methoxyl substitution of between about 19 to about 24 weight percent and a hydroxypropoxyl substitution of between about 4 to about 12 weight percent, based on the total weight of the water-soluble cellulose ether, which:
      i. has, as a 2 weight percent aqueous solution at 20° C., a viscosity of from about 50,000 mPa.s to about 600,000 mPa.s; and
      ii. has a particle size distribution, as measured prior to mixture with the other food ingredients, wherein at least about 40 weight percent of the water-soluble cellulose ether has a particle size from about 0.0006 meters to about 0.00025 meters, at least about 65 weight percent of the water-soluble cellulose ether has a particle size from about 0.0006 meters to about 0.00018 meters, and at least about 95 weight percent of the water-soluble cellulose ether has a particle size less than about 0.001 meters.

* * * * *